(12) United States Patent
Egeresi

(10) Patent No.: US 7,367,803 B2
(45) Date of Patent: May 6, 2008

(54) MULTI USER ORAL CLEANSING DEVICE, DENTALJET

(76) Inventor: Zoltan Egeresi, 5500 Coast Rd., Santa Cruz, CA (US) 95060

( * ) Notice: Subject to any disclaimer, the term of this patent is extended or adjusted under 35 U.S.C. 154(b) by 722 days.

(21) Appl. No.: 10/817,367

(22) Filed: Apr. 5, 2004

(65) Prior Publication Data

US 2004/0219483 A1     Nov. 4, 2004

(51) Int. Cl.
*A61H 9/00* (2006.01)
(52) U.S. Cl. .................. 433/80; 601/165; 601/162
(58) Field of Classification Search ............ 601/162, 601/165; 433/80; 239/101, 99
See application file for complete search history.

(56) References Cited

U.S. PATENT DOCUMENTS

| | | | | |
|---|---|---|---|---|
| 3,810,465 A | * | 5/1974 | Lambert | 601/160 |
| 3,902,664 A | * | 9/1975 | Deines | 239/99 |
| 3,973,558 A | * | 8/1976 | Stouffer et al. | 601/165 |
| 4,135,501 A | * | 1/1979 | Leunissan | 433/80 |
| 4,512,514 A | * | 4/1985 | Elcott | 239/99 |
| 4,942,870 A | * | 7/1990 | Damien | 601/165 |
| 5,095,893 A | * | 3/1992 | Rawden, Jr. | 601/165 |
| 5,218,956 A | * | 6/1993 | Handler et al. | 601/155 |
| 5,220,914 A | * | 6/1993 | Thompson | 601/155 |
| 5,387,182 A | * | 2/1995 | Otani | 601/165 |
| 5,727,733 A | * | 3/1998 | Ruttenberg | 239/99 |
| 6,740,053 B2 | * | 5/2004 | Kaplowitz | 601/162 |
| 6,848,471 B2 | * | 2/2005 | Floh et al. | 137/512.15 |

* cited by examiner

*Primary Examiner*—Ralph A. Lewis
(74) *Attorney, Agent, or Firm*—Zoltan Egeresi

(57) ABSTRACT

This invention creates a convenient low cost water pressure driven multi user oral cleansing device, the DentalJet with exchangeable color coded nozzle/handle which is easy to use, needs no electricity. The invention uses a faucet attachable rotating diverter, a flexible longer food grade PVC tube and interchangeable color coded jet nozzle/handle. The diverter also functions as a fine water volume/pressure control with a preset temperature and filter. Water pressure bulges up the flexible rubber tube clamped to the end of the adapter and to the PVC tubing. Inside the handle the water pressure created friction keeps the hose adapter in solid coupling while the pressure is on. The rubber tube oscillates, as pulsating water exist at the nozzle. When the water pressure is removed, color coded nozzle/handle is exchangeable.

2 Claims, 5 Drawing Sheets

(28) Canceled

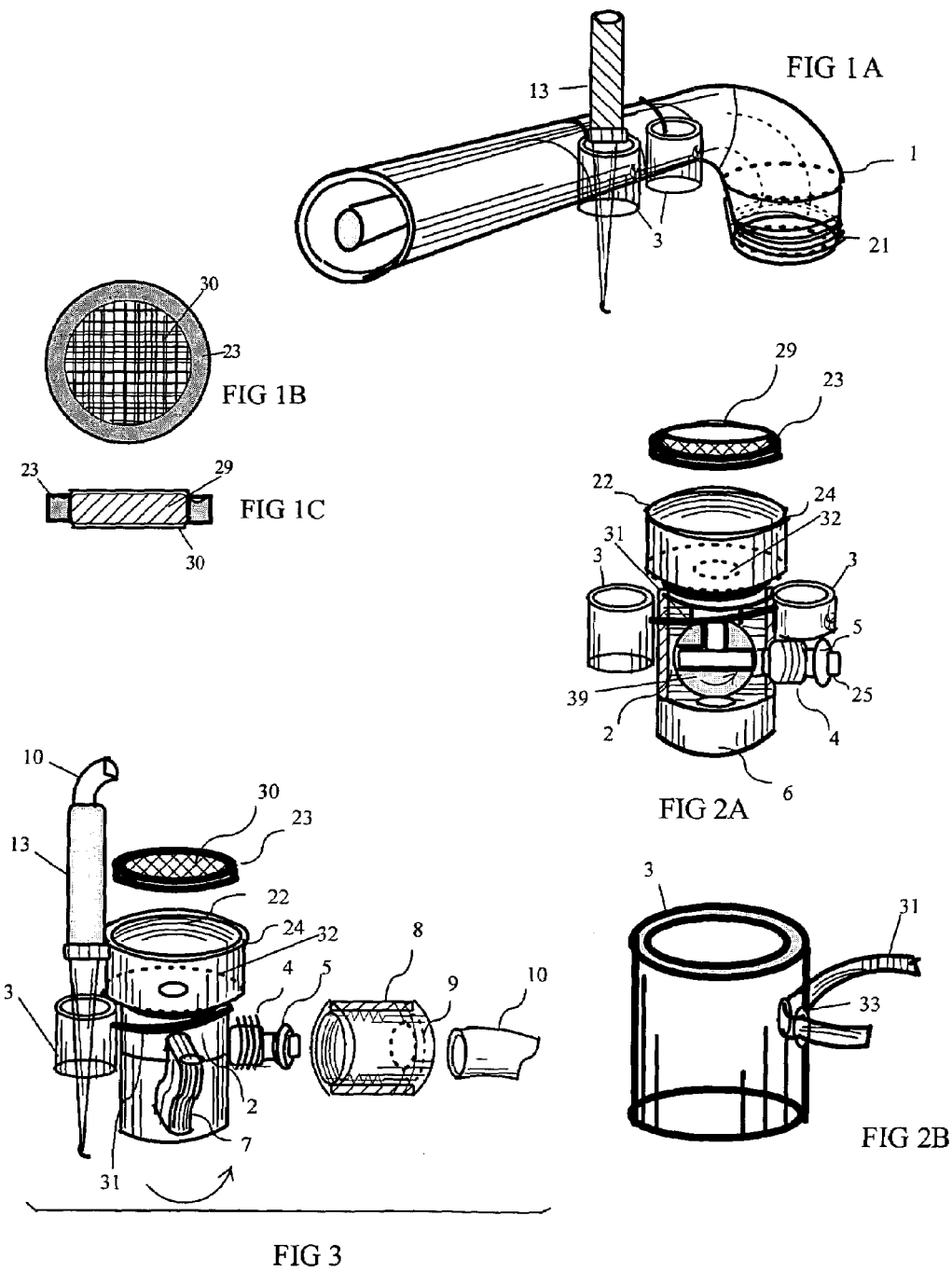

ary, DENTALJET

BACKGROUND OF THE INVENTION

1. Field of Invention

This invention generally relates to the field of dental hygiene; in particularly to the ways and means of removing- and, washing out food particles from the oral cavity, from under bridge works, around crowns, plaque from teeth and massaging gums in a user friendly, inexpensive way. This DentalJet is also useful for cleaning dentures, or even jewelry with the strong jet flow setting. Most attention has been given to the care and preservation of the teeth and gums, and to various types of apparatus employing a jet of water for cleaning the teeth and massaging the gums. Such apparatuses are old and well known in the arts and are generally characterized as being structurally complex, most are expensive to manufacture, some are big and bulky, unsightly or inconvenient to use.

2. Description of Prior Art

This multi user oral cleansing invention overcomes some of these shortcomings of the prior arts and creates a new way to maintain excellent oral hygiene at low cost in the most convenient way. U.S. Pat. No. 3,973,558 Stouffer et al uses an oscillating jet tip, nozzle/handle seems too long for practical use. U.S. Pat. No. 4,135,501 Leunissan uses an adapter gripping to the faucet, in most cases it would slip off from the water pressure, or it is not adaptable to most types of faucets. U.S. Pat. No. 4,942,870 Damien looks bulky and may be impractical for daily use and is not being marketed. U.S. Pat. No. 5,095,893 Rawden Jr. seems to be a low cost oral cleaning device; the diverter is a pull type. Once activated, water pressure keeps the diverter in diverted position, no secondary fine pressure adjustment is available but it employs a replaceable jet and pulsating impeller. U.S. Pat. No. 5,220,914 Thompson's water/antiseptic mixer, installed to the shower head or to cold water line. Otani uses snap on coupling which needs to be removed for regular faucet use. Several powered and non-powered dental cleaning devices have been invented. The only dental jet widely marketed is a powered multi nozzle Teledyne's Waterpik system and there is next to nothing on the non powered version; for the most part being impractical, inconvenient or cumbersome in design. My present invention contains none of the disadvantages of the prior art. It is a simple design and lacks moving parts or electricity. Safety and convenience is increased, while noise, cost and maintenance is reduced.

BRIEF SUMMARY OF THE INVENTION

The object of this invention is to create a new multi-user water pressure driven oral cleansing device with exchangeable nozzle/handle that is easy to use, uses no electricity, inexpensive to manufacture, and therefore is inexpensive at the retail level. This invention creates a more convenient way to maintain dental hygiene. Just by rotating the diverter; it turns a faucet into an inexhaustible water source for the DentalJet. It can be manufactured with few components, uses domestic water supply under pressure The object of this invention is to provide a new and convenient way to exchange nozzles for the different family members by using a pressurized flexible hose adapter with expendable rubber tubing inside the handle. Water flows in the flexible tubing, causing a pulsating jet stream as it bulges up the rubber hose around the adapter keeping it tight inside the handle. The color coded jet-tip/handle can be replaced when water pressure is removed by turning the diverter in the regular straight direction. Deflated rubber tubing allows an easy exchange of water jets by sliding the "interchangeable handle/DentaiJet" in and out.

The footprint of this DentalJet is very small. The handle holder is attached to the diverter, needs no extra counter space which is very important in small bathrooms, needs no electricity.

BRIEF DESCRIPTION OF THE SEVERAL VIEWS OF THE DRAWINGS

FIG. 1A typical faucet spout. FIGS. 1B and 1C illustrate a special filter washer (29).

FIG. 2A shows a prior art diverter (2) with a DentalJet holder (3) on the side.

FIG. 3 shows the DentalJet diverter in normal position.

DETAILED DESCRIPTION OF THE INVENTION

Figure 4:
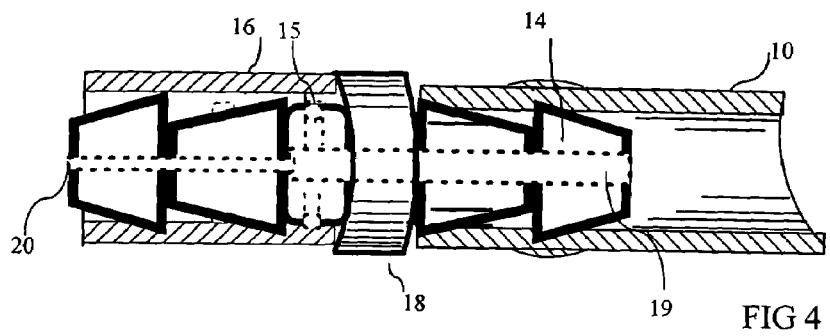
FIG. 4 shows the elected interchangeable hose assembly.

FIG. 1-3 illustrates prior art components as it is being used with the new invention. FIG. 1A shows a typical faucet spout (1) with threading (21), DentalJet (13) in the holder (3), 1B and 1C is a special filter/washer (23) with rubber vulcanized to the fine plastic filtering screen on top and on the bottom (30) with felt in the center (29) for fine particle filtering to prevent clogging up the DentalJet (13).

Figure 5:
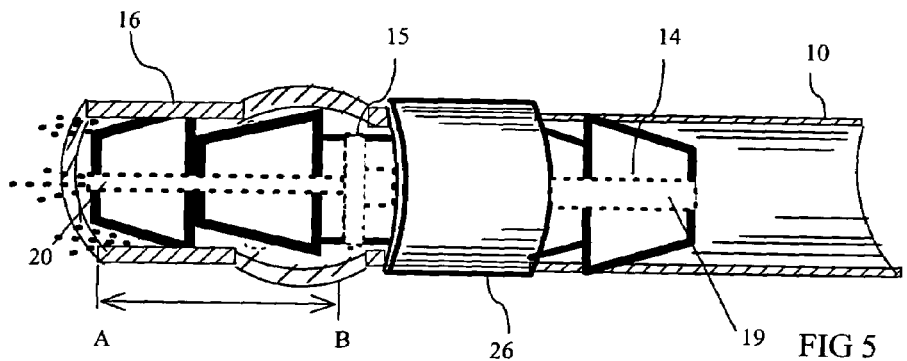
FIG. 5 illustrates the interchangeable hose assembly with a single, wide clamp (26) under water pressure, flexible rubber tube (16) is in the inflated position.
Figure 6:
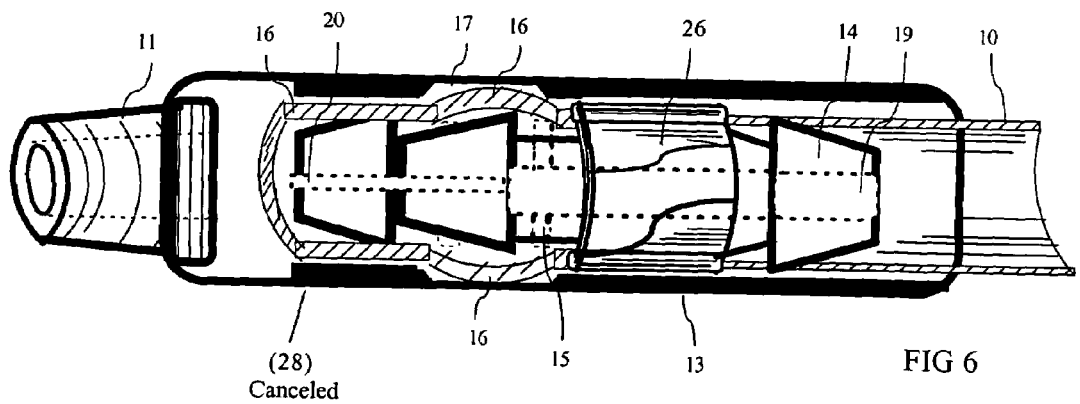
FIG. 6 shows the hose assembly in the inflated position inside the handle (13), the inside diameter of handle is enlarged (17) to accommodate the inflated rubber hose to keep the assembly inside the handle (13).

FIG. 2A shows the diverter (2) in diverted mode supplying water via filter (23), center of diverter (32) via rotating diverter drum (39) compression type connector (5), (25), threading (4), normal flow exists through regular aerator (6) from faucet (1). Diverter is attached to the end of the faucet by captive, rotating nut (24) with inside threading a DentaiJet holder (3) on the side, 2B shows the DentalJet holder (3) made of plastic, preferably PVC or vinyl. It has two oval holes (33) on the side, plastic cable tie (31) is threaded through and around the diverter above the diverter knob (7) to keep the DentalJet (13) in a secure position when not in use. FIG. 3 shows the diverter (2) in normal mode with flexible PVC tube (10) which is fed through compression nut (8) in the center hole (9) over the sleeve (5) to provide a water-tight connection when nut (8) is tightened, flex tube is about 20-25" long, the other end is the interchangeable hose assembly (FIGS. 4, 5, 6). Diverter knob (7) in partial diversion acts as a fine volume/pressure control, as it adjusts water pressure very conveniently with one hand with pre-selected water temperature.

FIG. 4 shows the other end of the flexible PVC hose (10) capable for compression and water tight barbed fitting at the interchangeable hose assembly, as it is tightly fitted on the rigid barbed connector (14) at least one inch in length. The other end of the adaptor has a flexible, expandable rubber tube (16) over the barbing area A to B attached with single clamp (18). Water flows from PVC hose (10) through the rigid, barbed adapter (14) intake opening (19) through smaller diameter volume limiter opening to the front end opening (20). The front end of the rigid plastic or metal barbed adapter (14) is drilled through at location (15) to channel the water under the flexible rubber hose (16). As the water flows under pressure through the opening (15) it bulges up the rubber tube (FIG. 4, 5, 6) and presses against the inner wall of the DentalJet at FIG. 6 (17) to keep the hose tip assembly solidly inside the interchangeable handle (13).

Front end of adapter (14) has some "play" inside the handle to allow some water to pass through between the barbing and the rubber hose. The bulged up tube releases some water on the front when pressure is built up, partially deflates as water exits, than bulges up again, providing an oscillating, pulsating water flow effect as the water flows into the jet tip (11) in the handle. On FIGS. 5 and 6 the clamp (26) is dual wide to be able to clamp the water supply hose (10) and the expandable short rubber hose (16) together to the barbed adapter (14).

Figure 7:
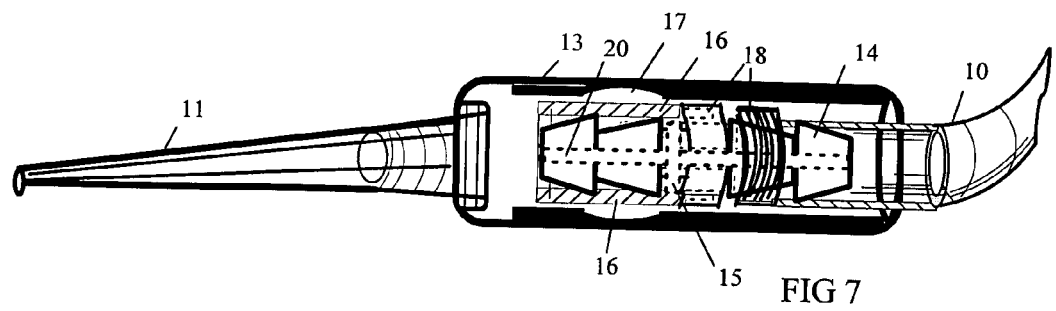
FIG. 7 shows the side view of the DentalJet with dual single clamps.

FIG. 7 shows the complete interchangeable nozzle/handle assembly with the adapter hose assembly inserted without water pressure.

Figure 8:
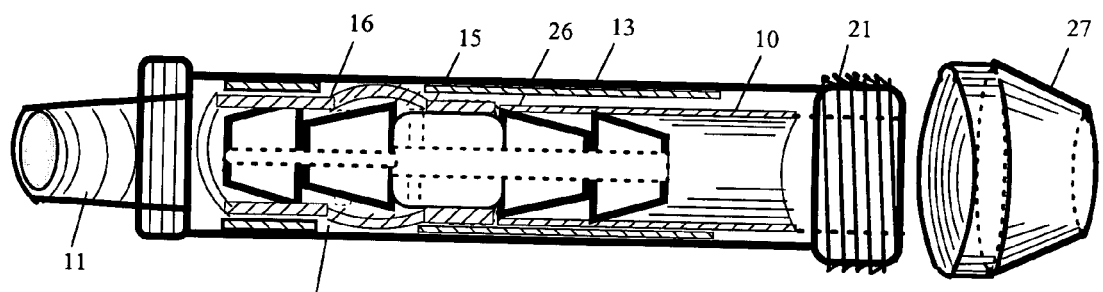
FIG. 8 side view shows the hose assembly inside the handle with a closing cap (27).

FIG. 8 is a preferred configuration for a single user, where the handle is threaded at the end (21) and closable by cap (27).

Figure 9:
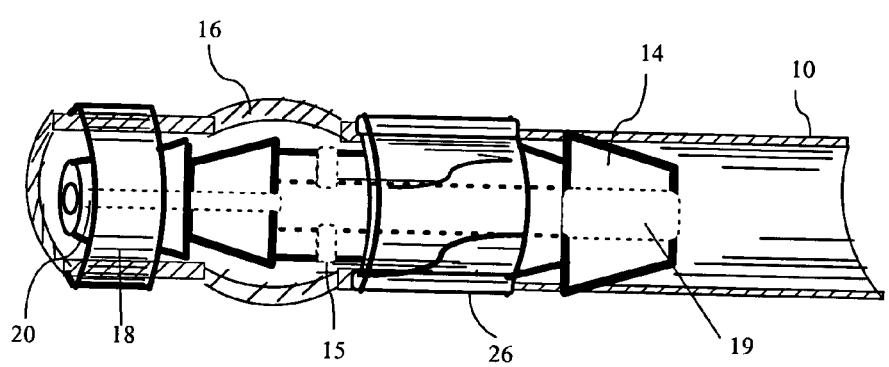
FIG. 9 shows the rubber hose end with two clamps providing the maximum tightness inside the handle, but no pulsating effect FIG. 10 same as FIG. 6 with nozzle (11) with maximum pulsating effect.
Figure 10:
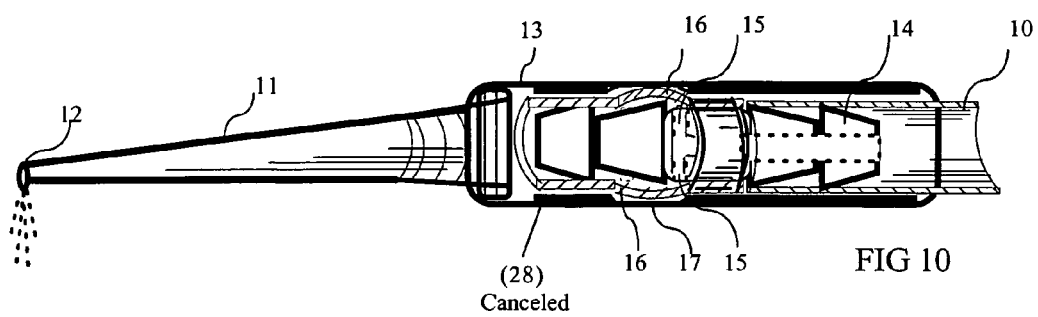

FIG. 9 shows a non pulsating interchangeable hose adapter end where the expandable rubber tube (16) is clamped at both end by clamps (18 and 26), providing the maximum friction to hold the hose adapter inside the handle (13) as water pressure bulges up the tube through the hole (15). FIG. 10 shows the maximum pulsating effect, all water passes under the flexible rubber hose (16) than to the nozzle (11).

Figure 11:
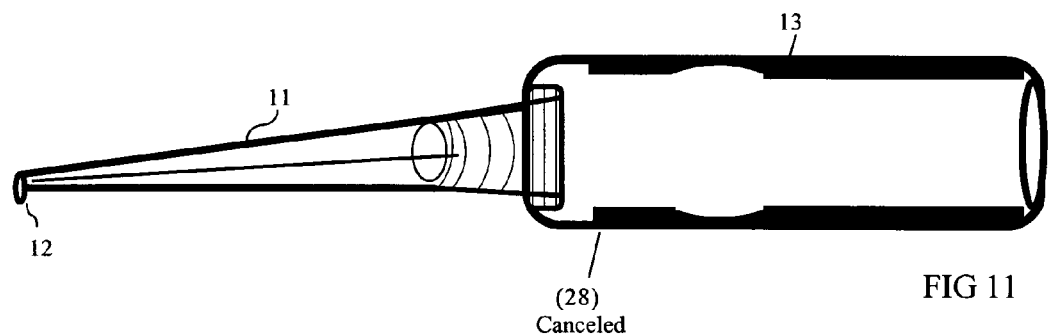
FIG. 11 shows the side view of the case (13) and tip (11) as a sealed unit.
Figure 12:
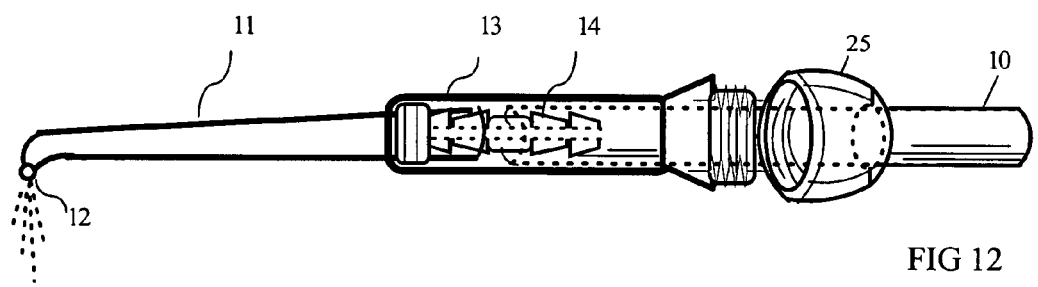
FIG. 12 shows the stainless steel barbed adapter (14) molded inside the PVC tip (11) for a single user.
Figure 13:
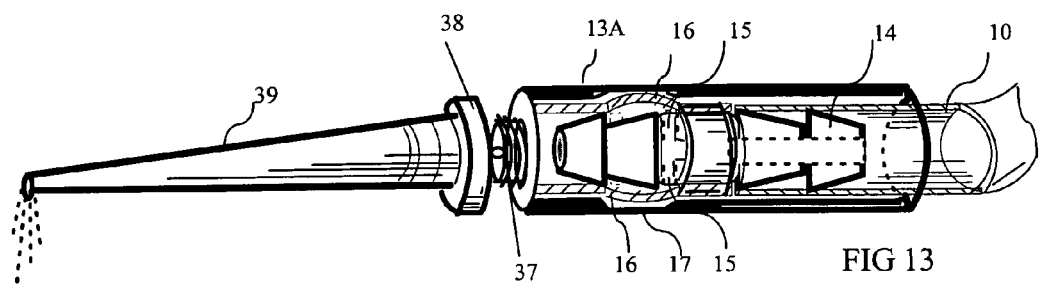
FIG. 13 shows a replaceable threaded nozzle (39) with pulsating adapter assembly/handle.

FIG. 11 shows the integrated nozzle/handle (11,13) nozzle (12) without the hose tip assembly. FIG. 12 shows a single user DentalJet assembly where one end of the brass or stainless steel adapter (14) is molded into the jet tip (11), PVC hose (10) is barbed fitted, case is closable by threaded cap (25).

of FIG. 13 shows an interchangeable handle 13A with male threading at the front end (37) with an interchangeable nozzle assembly (39), nozzle (12) and inside threaded connecting with an interchangeable nozzle assembly (39), nozzle (12) and inside threaded connecting end (38) capable to being attached to the handle by with means of threading.

Figure 14:
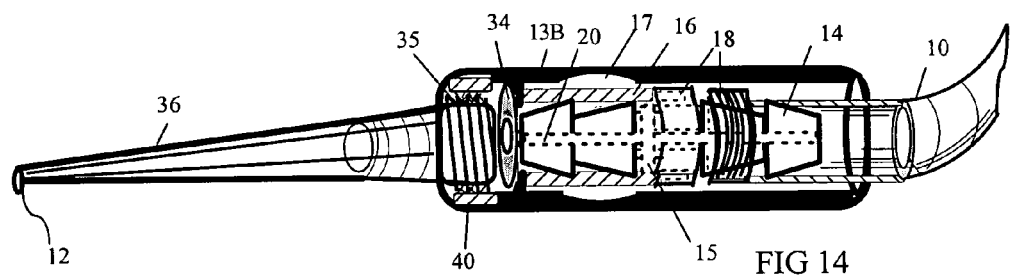
FIG. 14 the replaceable nozzle (36) with an exterior threading, it mates with the female threading of the handle as they are interchangeable.

FIG. 14 shows an interchangeable handle (13B) with an interchangeable nozzle adapter (36), where nozzle adapter has male threading at the end mating with the inside threading (41) of the (13B) handle, flat rubber washer (34) keeps tight water proof coupling.

In respect, after explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. It is important, therefore, that the claims be regarded as including such equivalent constructions insofar as they do not depart from the spirit and scope of the present invention, nor is it intended to be limiting as to the scope of the invention in any way.

The invention claimed is:

1. A multi-user oral cleansing device comprising:
    a diverter for connection to a faucet, said diverter having a valve for diverting water from the faucet;
    an elongated connecting hose having opposite first and second ends, said first end connected to the diverter for conveying water from the valve;
    a dental jet hand piece being connected to the second end of the elongated connecting hose and having a nozzle for directing fluid to a patient's oral cavity, said jet hand piece having an adapter for pulsating the flow of water through the jet hand piece, said adapter being comprised of an elongated rigid tubular member having barbed first and second ends and a first fluid passage extending longitudinally there through, said adapter further including a second fluid passage extending diagonally through the tubular member wall and in communication with the first fluid passage, said first barbed end being connected to the second end of the elongated connecting hose, said adapter further comprising a rubber hose that extends over the second barbed end of the tubular member and covers the second diagonal fluid passage;
    wherein when water flows through the jet handpiece water is conveyed through the adapter first passage and through the second passage where the water pressure repeatedly bulges the rubber hose around the tubular member second barbed end until the water is released out the end of the rubber hose and the bulging hose collapses, the repeated bulging and collapsing of the rubber hose causing the water directed out of the nozzle to pulsate.

2. A kit comprising the multi-user oral cleansing device of claim 1 further comprising:
    a plurality of color coded handle and nozzle members that are interchangeable over said adapter for use by other users.

* * * * *